United States Patent [19]
Clubb et al.

[11] Patent Number: 6,031,125
[45] Date of Patent: Feb. 29, 2000

[54] PROCESS OF USING A SOLUBLE MAGNESIUM CATALYST FOR PREPARATION OF DIHYDROXY ESTERS

[75] Inventors: Clyde Neal Clubb; Thomas James Devon; Garrett Clements Luce, all of Longview, Tex.

[73] Assignee: Eastman Chemical Company, Kingsport, Tenn.

[21] Appl. No.: 09/131,179

[22] Filed: Aug. 10, 1998

Related U.S. Application Data

[62] Division of application No. 08/642,376, May 3, 1996, Pat. No. 5,861,354.

[51] Int. Cl.$^7$ .................................................. C07C 69/66
[52] U.S. Cl. ............................................................ 560/182
[58] Field of Search ............................................... 560/182

[56] References Cited

U.S. PATENT DOCUMENTS

| | | |
|---|---|---|
| 3,852,335 | 12/1974 | Merger et al. . |
| 3,862,215 | 1/1975 | Merger et al. . |
| 4,851,592 | 7/1989 | Morris et al. . |
| 5,041,621 | 8/1991 | Morris et al. . |
| 5,380,919 | 1/1995 | Merger et al. ........................... 560/179 |

*Primary Examiner*—Gary Geist
*Assistant Examiner*—Robert W. Deemie
*Attorney, Agent, or Firm*—Rose M. Allen; Harry J. Gwinnell

[57] ABSTRACT

A catalyst and process for preparation of dihydroxy esters from specified hydroxy aldehydes is disclosed. In one embodiment, a catalyst liquid is provided which comprises from 10 percent to 60 percent magnesium salt of a specified alkanoic acid or acids, and from 90 percent to 40 percent of a particular alkanoic acid or acids, the molar ratio of alkanoic acid to magnesium salt being from about 1.5 to 20.3. The catalyst solution or liquid contacts or is contacted with a specified hydroxy aldehyde under suitable reaction conditions to form the desired dihydroxy ester. In another embodiment, dihydroxy esters are derived from specified hydroxy aldehydes by first forming a magnesium catalyst containing liquid by reacting magnesium or magnesium oxide, under suitable conditions, with a suitable alkanoic acid or acids, the acid or acids being provided in excess in specified molar ratios. The magnesium salt-alkanoic acid liquid produced is then employed as a catalyst liquid to convert the respective hydroxy aldehyde under suitable reaction conditions to form the desired dihydroxy ester.

26 Claims, No Drawings

PROCESS OF USING A SOLUBLE MAGNESIUM CATALYST FOR PREPARATION OF DIHYDROXY ESTERS

This Appln is a Division of U.S. Ser. No. 08/642,376 filed May 3, 1996, U.S. Pat. No. 5,681,354.

FIELD OF THE INVENTION

The invention relates generally to the conversion of hydroxy aldehydes to dihydroxy esters, and, more particularly, to the conversion of hydroxy aldehydes to dihydroxy esters in the presence of a magnesium-containing catalytic agent.

BACKGROUND OF THE INVENTION

The use of magnesium or magnesium-containing compounds to catalyze the conversion of hydroxy aldehydes to dihydroxy esters by the so-called Tishchenko reaction is known. Thus, magnesium ethyl iodide has been used to catalyze this reaction, as described by Franke and Kohn in *Monatsheft Fur Chemie*, vol. 25, page 865 (1904).

More recently, U.S. Pat. No. 3,852,335 (Merger et al) discloses the conversion of hydroxypivaldehyde using hydroxides, oxides, and hydrated oxides of various metals, such as magnesium, in anhydrous medium or with addition of water. U.S. Pat. No. 3,862,215 (Merger et al) discloses the use of solid magnesium hydroxide and magnesium oxide for the conversion of hydroxy aldehydes to dihydroxy esters, the catalysts being "advantageously used in finely divided form". Even more recently, U.S. Pat. No. 5,041,621 (Morris and Luce) discloses the production of dihydroxy esters from specified hydroxy aldehydes utilizing a catalytically active elemental metal selected from magnesium, zinc, manganese, aluminum, titanium, or calcium. According to the last-mentioned patent, only small amounts of the metal (preferably magnesium) are required, and the metal is introduced into the reaction zone as a powder.

The addition to and use of solid catalyst materials, such as metal or metal oxide powders, in the hydroxy aldehyde reaction liquid, suffer from a number of disadvantages. For example, powders present difficulties in handling, are not easily metered into the reaction zone, and are often removed from the product mixture only with difficulty. In addition, they may deposit in quiescent areas of the reaction zone, and, unless eventually partially or fully dissolved in the reaction liquid, require effort to maintain adequate distribution thereof in the liquid. In short, a catalyst and procedure for the production of dihydroxy esters that avoided or minimized the difficulties associated with solid catalysts might have great economic value. The invention is such a catalyst and procedure.

SUMMARY OF THE INVENTION

Accordingly, in one embodiment, the invention relates to a novel catalyst liquid for conversion of hydroxy aldehydes which comprises a solubilized magnesium component and an alkanoic acid or acids, in specified proportions. More particularly, the invention relates to a catalyst liquid comprising or containing from about 10 weight percent to about 60 weight percent of the magnesium salt or salts of an alkanoic acid having or containing from 2 through 8 carbon atoms or of a mixture of such acids; and from about 40 weight percent to about 90 weight percent of an alkanoic acid containing from 2 through 8 carbon atoms, or mixture of such acids; the molar ratio of such acid or acids to the magnesium salt or salts being from about 1.5 to about 20.3, preferably from about 2.5 to about 10. As used hereinafter and in the claims, the term "salt" of magnesium is understood to include the plural, i.e., more than one such composition, and is employed in a broad sense, i.e., including, but not limited to, a compound or compounds that result from the replacement of the acid hydrogen of the acid or acids mentioned by reaction with elemental magnesium and/or magnesium ion from compounds of magnesium, from the reaction of magnesium ion or compound(s) containing magnesium ion with a compound or compounds which provide an anion or anions which may be considered the anionic residue(s) of an alkanoic acid or acids of the type mentioned, or from other suitable reaction, such as by oxidation of an appropriate magnesium compound.

In a preferred embodiment, the invention relates to a catalyst liquid comprising or containing from about 10 weight percent to about 60 weight percent of magnesium isobutyrate, and from about 40 weight percent to about 90 weight percent of isobutyric acid, the molar ratio of the isobutyric acid to magnesium isobutyrate being from about 1.5 to about 20.3, preferably from about 2.5 to about 10. The catalyst liquids of the invention are effective for hydroxy aldehyde conversion in the absence of solid catalytic materials such as solid magnesium or magnesium oxide. Unless stated otherwise or inconsistent with context, all percentages or ratios expressed herein are by weight, based on the total weight of the composition involved.

In a further embodiment, the invention relates to a process for preparing certain dihydroxy esters from hydroxy aldehydes by contacting the respective hydroxy aldehydes with a catalytic amount of magnesium supplied as the magnesium salt of the acid or acids mentioned in liquid solution, in the absence of solid magnesium, under suitable reaction conditions. The di-hydroxy ester formed may be recovered or separated from the dissolved magnesium compound catalyst and any unconverted hydroxy aldehyde. The catalytic solution preferably comprises a liquid comprising or containing from about 10 percent to about 60 percent of the magnesium salt of said acid or acids, most preferably magnesium isobutyrate, and from about 40 percent to about 90 percent of the mentioned alkanoic acid, or acids, most preferably isobutyric acid, the molar ratio of the acid or acids to magnesium salt being from about 1.5 to about 20.3, preferably from about 2.5 to about 10.

In yet another embodiment, the invention relates to a process for preparing specified dihydroxy esters from hydroxy aldehydes comprising providing a catalyst liquid comprising or containing the aforementioned magnesium salt and alkanoic acid or acids, preferably magnesium isobutyrate and isobutyric acid, respectively, in the ratios mentioned. An amount of the magnesium salt-alkanoic acid containing liquid sufficient to provide a catalytic amount of solubilized magnesium then contacts or is then contacted with the respective hydroxy aldehyde under reaction conditions to form the desired dihydroxy ester. In still a further embodiment, specified dihydroxy esters are derived from hydroxy aldehydes by first forming a magnesium salt-alkanoic acid or salt-alkanoic acids containing liquid by reacting magnesium or reactive magnesium compound, such as magnesium oxide, with the specified alkanoic acid or acids, the acid or acids being provided in limited excess. Magnesium salt-acid or salt-acids containing solution or liquid so produced then is employed as a catalyst solution or liquid to convert the respective hydroxy aldehyde under suitable reaction conditions to form the desired dihydroxy ester. Each of the embodiments mentioned is particularly adapted to conversion of hydroxypivaldehyde, the dihydroxy ester formed being hydroxypivalyl hydroxypivalate, the preferred alkanoic acid being in each case isobutyric acid. The invention thus provides a catalytic liquid which is easily handled, easily metered into the reaction solution, and, being soluble in the reaction liquid, is easily distributed therein.

DETAILED DESCRIPTION OF THE INVENTION

The hydroxy aldehydes employed in the invention are selected from those compounds having the formula

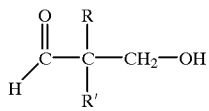

wherein R and R' are independently selected from $C_1$ through $C_4$ alkyl. The reaction, therefore, is shown as

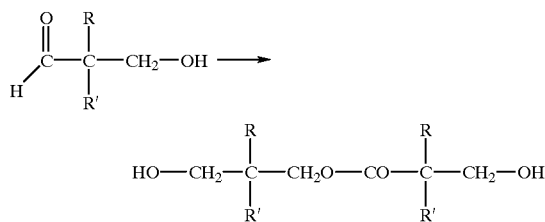

wherein R and R' have the values stated. The hydroxy aldehyde need not be pure, so long as any component therein does not interfere significantly with the conversion reaction or the catalyst. Crude hydroxy aldehyde streams, exemplified here-inafter, may be used, or process streams containing more than one hydroxy aldehyde or already containing some product, are within the invention.

As indicated, R and R' are preferably methyl, so that the preferred hydroxy aldehyde for conversion is hydroxypivaldehyde, the ester formed being hydroxypivalyl hydroxypivalate. Hydroxypivaldehyde used as starting material may be prepared from isobutyraldehyde and aqueous formaldehyde in the presence of a suitable catalyst, such as a trialkylamine, NaOH, or $Na_2CO_3$, under known reaction conditions, and both the crude product from this reaction and the purified hydroxypivaldehyde are suitable as starting materials. In a preferred embodiment, the novel catalytic liquid of the invention may be supplied to a drying zone, for example, to the base of a drying column, while crude hydroxypivaldehyde, which contains water, is supplied, for example, to the middle of the column. The crude hydroxypivaldehyde is heated to, e.g., 50° C. to 150° C., to remove water, and the catalytic liquid of the invention promotes the conversion reaction in the lower part of the column. This immediate catalytic action enhances any spontaneous conversion and allows the possibility of elimination of a reactor or reaction zone for the hydroxyaldehyde conversion, which commonly requires more than one conversion reactor or zone for adequate residence time.

As mentioned, the catalyst liquid containing magnesium salt of a specified alkanoic acid and certain alkanoic acid or acids is supplied to or in the hydroxy aldehyde in an amount to provide solubilized magnesium in a catalytic amount. While even a minimal amount of the magnesium salt containing liquid of the invention will have some effect, the catalyst liquid normally will be supplied to or contacts the hydroxy aldehyde in a catalytic amount, i.e., an amount sufficient to provide significant conversion of the hydroxy aldehyde. In general, the catalyst liquid will be supplied in an amount sufficient to provide a magnesium ion concentration in the hydroxy aldehyde of at least 10 ppm. Preferably, a magnesium ion concentration of 20 to 1000 ppm, most preferably 40 to 100 ppm, will be employed, although substantially larger amounts of magnesium may be used, if desired. Proportions of magnesium salt to alkanoic acid or acids may be varied within the ranges specified, and other non-interfering components, such as solvents, may be present, even in significant amounts, provided the ratio of magnesium salt of the alkanoic acid or acids to alkanoic acid or acids specified is maintained and liquidity is not compromised. For example, a non-interfering solvent such as methanol or 2,2,4-trimethyl-1,3-pentanediol monoisobutyrate may be present in an amount up to 50 percent, with an amount of from 0.001 percent to 20 percent being tolerable. However, compositions consisting essentially of magnesium salt of the specified alkanoic acid or acids, and the mentioned alkanoic acid or acids, in the proportions and ratios mentioned, are preferred in the invention.

As indicated, the acid component employed in conjunction with the magnesium salt of the specified alkanoic acid or acids is selected from alkanoic acids containing from 2 through 8 carbon atoms, or a mixture of such acids. Suitable alkanoic acids include acetic acid, propionic acid, butyric acid, isobutyric acid, valeric acid, isovaleric acid, hexanoic acid, and octanoic acid. Isobutyric acid is preferred.

In most cases, to provide a liquid catalyst solution of magnesium salt of alkanoic acid or acids in the specified alkanoic acid or acids, the salt, which is normally a solid, may simply be dissolved in the specified acid or acids. For example, to provide a liquid catalyst solution of magnesium isobutyrate with or in isobutyric acid, solid magnesium isobutyrate may be dissolved in isobutyric acid, by the addition of heat, if necessary, in the ratios mentioned. While some salt-acid or acids combinations within the scope of the range specified may be solid at room temperatures, gentle heating, preferably to the temperature employed in the hydroxy aldehyde conversion zone, will normally be sufficient to liquefy the combination material. Alternatively, the magnesium salt-alkanoic acid or acids-containing liquid may be prepared by reacting magnesium or a reactive magnesium compound with a stoichiometric excess of the alkanoic acid or acids under suitable conditions. In the case of elemental magnesium, the metal, preferably as turnings, is mixed with the acid or acids under conditions to react the magnesium and the acid(s). In general, most of the salt forming reactions proceed spontaneously, so that room temperature and atmospheric pressure are sufficient to obtain combination. In the case of magnesium and isobutyric acid, for example, the isobutyric acid is supplied in excess of the stoichiometric amount with respect to the magnesium metal, so that magnesium consumption is complete and separation of any remaining magnesium is unnecessary. Preferably, the isobutyric acid is supplied in sufficient excess to the effect that the reaction mixture containing magnesium isobutyrate remains a liquid. In general, the alkanoic acid or acids utilized are supplied in excess for reaction with the magnesium in a ratio of from about 3.5 to 24.6, preferably 4.7 to 7.3, on a molar basis. This liquid solution, containing the dissolved magnesium salt, may then be employed directly in the conversion of the hydroxy aldehyde.

The magnesium salt may also be prepared by reaction of the mentioned alkanoic acid or acids with one or more reactive magnesium compounds. As used herein, the term 'reactive magnesium compound' refers to any magnesium compound which has significant reactivity with the particular alkanoic acid or acids, provided the anionic residue of the compound, if any, does not interfere substantially with the hydroxyaldehyde conversion reaction, or, if interfering, is easily removed or otherwise rendered non-interfering. A plurality of such compounds may also be used to form the salt, i.e., a mixture of 'reactive magnesium compounds' may be employed. Within the considerations mentioned, a wide variety of magnesium compounds may be selected by those skilled in the art, including, but not limited to, magnesium oxide, magnesium chloride, magnesium bromide, magnesium carbonate(s), magnesium acetate, magnesium citrate, magnesium formate, magnesium propionate, and magnesium acetylacetonate. Magnesium oxide or precursors thereof are preferred. The magnesium salt-alkanoic acid(s) solution is easily prepared by heating the reactive magnesium compound or mixture of compounds with a stoichiometric excess of the alkanoic acid or acids. For example, in the case of magnesium oxide-isobutyric acid, the isobutyric acid will normally be supplied, with respect to the magnesium oxide, in excess in a ratio of from about 3.5 to 24.6, preferably 4.7 to 7.3, on a molar basis. Heating in the range of from 60° C. to about 200° C. will normally suffice to complete the reaction, although those skilled in the art may vary these conditions as appropriate, and the catalyst may then be used in the hydroxy aldehyde. Reactive magnesium compound from any suitable source may be employed. While the reactive magnesium compound or compounds need not be 'pure', better grade material, such as C.P. grade MgO, is preferred. Similarly, the source of the alkanoic acid or acids is not critical. In all cases, if large particles or large excesses of magnesium or reactive magnesium compound(s) are employed, the crude magnesium salt-acid(s) solution is preferably filtered before use.

The magnesium salt of the alkanoic acid chosen may also be prepared by reacting magnesium containing compound(s) with a compound or compounds containing an anion or anions which are the residues of suitable alkanoic acid or acids and whose cation or cations are displaceable by magnesium, e.g., ammonium isobutyrate. After separation, the magnesium salt may then be combined with the specified alkanoic acid or acids, as mentioned.

The combining or contacting of the hydroxyaldehyde and magnesium salt-alkanoic acid(s) liquid is carried out under reaction conditions to form the dihydroxy ester, i.e., those conditions of temperature, pressure, length of contact time, etc., which enable or allow the reaction to proceed with formation of the dihydroxy ester. Included in such conditions are those required to supply or to maintain the hydroxy aldehyde in the liquid phase, i. e., temperature and pressure, so that intimate contact with the magnesium salt-acid(s) containing liquid is realized. Suitable temperatures, for example, may range from 50° C. to 150° C., preferably from 80° C. to 120° C. Pressures may be varied considerably, and may range, for example, from 0.1 atmosphere to 4 atmospheres, preferably 1 atmosphere to 2 atmospheres. For a batch reaction, total reaction times, i.e., the time to completion or desired rate of completion of the conversion, will vary considerably, but in general will range from 0.5 hour to 15 hours or so, preferably from 2 hours to about 8 hours. In the case of a continuous process, with continuous feed to a reaction zone and continuous withdrawal of product containing mixture, average contact time may range from about 0.5 hour to 15 hours, preferably from about 2 hours to about 8 hours, contact time herein being understood as the liquid volume in the reactor divided by the volumetric flow rate of the liquid. Reaction temperatures will preferably range from 50° C. to 150° C., most preferably 80° C. to 120° C. Pressures may range from about 0.1 atmosphere to 4 atmospheres, preferably 1 atmosphere to 2 atmospheres. Reaction conditions in the presence of magnesium isobutyrate generally comprise mild temperatures and pressures, well within the ranges mentioned.

While the conversion may be carried out either on a batch or continuous basis, the invention is admirably suited to a continuous reaction process. In this latter preferred case, the hydroxy aldehyde and solublized magnesium are introduced, on a continuous basis, into a reaction zone maintained under the appropriate reaction conditions, the hydroxy aldehyde-magnesium salt-acid(s) mixture, with forming reaction products, passing through and eventually being removed from the reaction zone. The degree of completion of the reaction is dependent on the conditions above-mentioned, the resultant reaction product mixture being removed at an outlet of the reaction zone. The magnesium salt of the alkanoic acid(s) and unconverted hydroxy aldehyde may be recovered or separated by known procedures, e.g., by distillation with a thin film evaporator, as described in U.S. Pat. No. 5,209,827.

The following experiments were conducted.

I

Ten grams (0.41 mol) of magnesium metal turnings were placed on a glass frit above the liquid level of a Soxhlet extractor, and 200 grams of isobutyric acid were heated to reflux for 2 hours in the extractor. The magnesium turnings reacted fully with the condensed reflux vapor, and the magnesium isobutyrate formed dissolved in the refluxing liquid. Cooling of the liquid gave a glassy material which could be reliquified by heating the material on a steam bath. About 10 milliliters of this solution, which assayed at about 39.0 percent magnesium isobutyrate, were added to 200 milliliters of acetone, precipitating a white powder.

The powder was washed with an additional 100 milliliters of acetone and then dried to leave 1.9 grams of white powder magnesium isobutyrate.

Further, ten grams of magnesium oxide (0.25 mol) were heated with 88 grams (1.0 mol) of isobutyric acid at 120° C. for four hours. The resulting solution was filtered to remove particulates, and was titrated with dilute HCl to determine magnesium isobutyrate assay. The materials prepared were then evaluated in the following manner. In each evaluation experiment, sufficient material was combined in a batch reactor, in the manner indicated hereinafter, with 150 grams of a sample of dry, crude hydroxypivaldehyde, which already contained some hydroxypivalyl hydroxypivalate, to give a catalyst concentration of 120 ppm of magnesium. Heat was applied, and after an initial exotherm in each case, the reaction temperature was held at 115° C. for the duration of the experiment. Samples were taken periodically, and were analyzed by gas chromatography for hydroxypivalyl hydroxypivalate concentration. For comparison, this procedure was also conducted without a catalyst, and separately with magnesium isobutyrate powders. The results are shown in Table I.

TABLE I

| Sample | hydroxypivalyl hydroxypivalate (%) Time (min.) | | | |
|---|---|---|---|---|
| | 0 | 30 | 60 | 120 |
| 1. 50% magnesium isobutyrate/ isobutyric acid | 15.7 | 42.2 | 50.8 | 60.3 |
| 2. 39% magnesium isobutyrate/ isobutyric acid | 15.7 | 56.0 | 64.2 | 67.5 |
| 3. 33% magnesium isobutyrate/ isobutyric acid, from MgO, dried | 9.2 | 58.8 | 66.8 | 70.4 |
| 4. 33% magnesium isobutyrate/ isobutyric acid, from MgO, wet | 9.2 | — | 67.7 | 70.7 |
| 5. 100% magnesium isobutyrate from Mg metal (white powder) | 15.7 | 61.3 | 62.9 | 62.5 |
| 6. 100% magnesium isobutyrate from MgO (mostly soluble) | 15.9 | — | 45.0 | 58.3 |
| 7. 0% magnesium isobutyrate (no catalyst) | 15.7 | 32.3 | 35.5 | 41.7 |

As will be appreciated by those skilled in the art, the catalyst liquids of the invention demonstrate good activity, with 60 percent to 70 percent hydroxypivalyl hydroxypivalate production after two hours. Variability in conversion may be attributable to temperature variations since the catalysts tended to have large exotherms on catalyst addition. Activity of magnesium isobutyrate prepared from magnesium oxide was comparable to that made from magnesium turnings.

II

In order to evaluate the effects of temperature, catalyst concentration, and amount of excess isobutyric acid, additional batch experiments were conducted varying these parameters. In the first set of runs, the catalyst was prepared from prilled magnesium oxide to produce a liquid containing 51.6 % magnesium isobutyrate in isobutyric acid. The results are shown in Table II, the results given in the column labeled 'Initial' being observed before reaching the desired temperature.

TABLE II

| Mg. | Excess | Temp. | hydroxypivalyl hydroxypivalate (%) Time (min.) | | | |
|---|---|---|---|---|---|---|
| ppm | acid % | °C. | Initial | 120 | 240 | 360 |
| 30 | 0.023 | 105 | 26.25 | 59.32 | 71.67 | 76.87 |
| 44 | 0.047 | 105 | 26.25 | 61.18 | 70.82 | 74.31 |
| 45 | 0.047 | 100 | 26.25 | 45.88 | 54.59 | 61.78 |

Further runs were made with catalyst prepared from magnesium oxide (Strem) to produce a catalyst liquid containing 40.1 % magnesium isobutyrate in isobutyric acid. The results are shown in Table IIA, the results given in the column labeled 'Initial' being made after reaching the desired temperature.

TABLE IIA

| Mg. | Excess | Temp. | hydroxypivalyl hydroxypivalate (%) Time (min.) | | | |
|---|---|---|---|---|---|---|
| ppm | acid % | °C. | Initial | 120 | 240 | 360 |
| 0 | 0 | 105 | 27.9 | 37.3 | 43.64 | — |
| 49 | 0.072 | 105 | 28.9 | 77.8 | 78.2 | 80.4 |
| 96 | 0.14 | 105 | 58.8 | 74.7 | 78.2 | 80.4 |

III

In order to evaluate the effects of added acid and water upon hydroxy aldehyde conversion, additional batch experiments were conducted varying these parameters. In this set of runs, the catalyst liquid corresponded to that of the experiments of Table II (51.6 percent magnesium isobutyrate in isobutyric acid) and temperature was 105° C. The results are shown in Table III, the results given in the column labeled 'Initial' being made before reaching the desired temperature.

TABLE III

| Mg. | Excess | Temp. | hydroxypivalyl hydroxypivalate (%) Time (min.) | | | |
|---|---|---|---|---|---|---|
| ppm | acid % | °C. | Initial | 120 | 240 | 360 |
| 58 | 0 | — | 23.19 | 66.72 | 72.75 | — |
| 129 | 0 | — | 22.51 | 77.63 | 79.6 | 81.32 |
| 72 | 0.039 | — | 23.19 | 62.77 | 69.01 | — |
| 82 | 0.039 | — | 22.51 | 67.51 | 74.68 | 76.25 |
| 68 | 0.12 | — | 23.19 | 57.86 | 66.38 | — |
| 73 | 0.2 | — | 23.19 | 45.4 | 55.38 | — |
| 79 | 0.37 | — | 22.51 | 39.54 | 51.27 | 56.64 |
| 80 | 0.039 | 0.33 | 23.19 | 57.21 | 63.99 | — |

While the invention has been illustrated with particular compositions and apparatus, those skilled in the art will appreciate that equivalent or analogous compositions and apparatus may be employed. The term 'zone', as employed in the specification and claims, includes, where suitable, the use of segmented equipment operated in series, or the division of one unit into multiple units because of size constraints, etc.

What is claimed is:

1. A process for the preparation of a dihydroxy ester of the formula

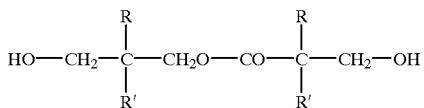

wherein R and R' are independently selected from $C_1$ through $C_4$ alkyl, comprising contacting a hydroxy aldehyde having the formula

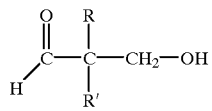

wherein R and R' are independently selected from $C_1$ through $C_4$ alkyl, with a catalytic amount of magnesium supplied as the magnesium salt of an alkanoic acid containing from 2 through 8 carbon atoms, or mixtures of such acids, in liquid solution, in the absence of solid magnesium or magnesium oxide, under reaction conditions to form said dihydroxy ester.

2. The process of claim 1 wherein the salt is magnesium isobutyrate and the liquid solution comprises isobutyric acid.

3. The process of claim 1 wherein the liquid solution comprises from about 10 percent to about 60 percent of the magnesium salt and from about 90 percent to about 40 percent of an alkanoic acid containing from 2 through 8 carbon atoms, or mixture of such acids, the molar ratio of the acid or acids to the magnesium salt being from about 1.5 to about 20.3; and the dihydroxy ester is recovered.

4. The process of claim 3 wherein the salt is magnesium isobutyrate and the alkanoic acid is isobutyric acid.

5. A process for the preparation of a dihydroxy ester of the formula

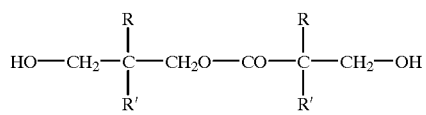

wherein R and R' are independently selected from $C_1$ through $C_4$ alkyl, comprising providing a catalyst liquid containing from about 10 percent to about 60 percent of the magnesium salt of an alkanoic acid containing from 2 through 8 carbon atoms, or mixture of such acids; and from about 40 percent to about 90 percent of an alkanoic acid containing from 2 through 8 carbon atoms, or mixture of such acids, the molar ratio of such acid or acids to the magnesium salt being from about 1.5 to about 20.3; contacting a hydroxy aldehyde having the formula

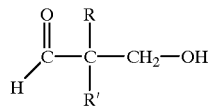

wherein R and R' are independently selected from $C_1$ through $C_4$ alkyl, with a catalytic amount of said catalyst liquid, under reaction conditions to form said dihydroxy ester.

6. The process of claim 5 wherein the salt is magnesium isobutyrate and the acid is isobutyric acid.

7. A process for the preparation of a dihydroxy ester of the formula

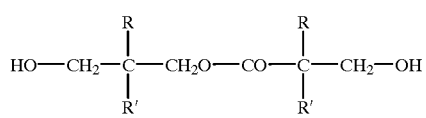

wherein R and R' are independently selected from $C_1$ through $C_4$ alkyl, comprising contacting elemental magnesium with a stoichiometric excess of alkanoic acid containing from 2 through 8 carbon atoms, or mixture of such acids, under reaction conditions to produce a catalyst liquid containing from about 10 percent to about 60 percent of the magnesium salt of an alkanoic acid containing from 2 through 8 carbon atoms, or mixture of such acids, and from about 40 percent to about 90 percent of an alkanoic acid containing from 2 through 8 carbon atoms, or mixture of such acids, the molar ratio of such acid or acids to the magnesium salt being from about 1.5 to about 20.3; contacting a hydroxy aldehyde having the formula

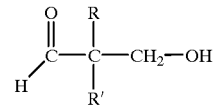

wherein R and R' are independently selected from $C_1$ through $C_4$ alkyl, with a catalytic amount of said catalyst liquid, under reaction conditions to form said dihydroxy ester.

8. The catalyst liquid of claim 7 wherein the salt is magnesium isobutyrate and the acid is isobutyric acid.

9. A process for the preparation of a dihydroxy ester of the formula

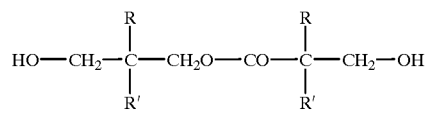

wherein R and R' are independently selected from $C_1$ through $C_4$ alkyl, comprising contacting a reactive magnesium compound or mixture of reactive magnesium compounds with a stoichiometric excess of an alkanoic acid containing from 2 through 8 carbon atoms, or mixture of such acids, under reaction conditions to produce a catalyst liquid containing from about 10 percent to about 60 percent of the magnesium salt of an alkanoic acid containing from 2 through 8 carbon atoms, or mixture of such acids; and from about 90 percent to about 40 percent of an alkanoic acid containing from 2 through 8 carbon atoms, or mixture of such acids, the molar ratio of acid or acids to magnesium salt being from about 1.5 to about 20.3; contacting a hydroxy aldehyde having the formula

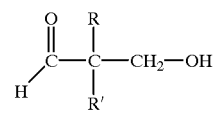

wherein R and R' are independently selected from $C_1$ through $C_4$ alkyl, with a catalytic amount of said catalyst liquid, under reaction conditions to form said dihydroxy ester.

10. The catalyst liquid of claim 9 wherein the salt is magnesium isobutyrate and the acid is isobutyric acid.

11. A process for the preparation of a dihydroxy ester of the formula

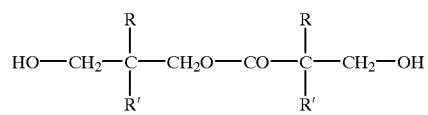

wherein R and R' are independently selected from $C_1$ through $C_4$ alkyl, comprising contacting magnesium oxide with a stoichiometric excess of an alkanoic acid containing from 2 through 8 carbon atoms, or a mixture thereof under reaction conditions to form a catalyst liquid containing from about 10 percent to about 60 percent of the magnesium salt of alkanoic acid containing from 2 through 8 carbon atoms, or mixture of such acids, and from about 40 percent to about 90 percent of an alkanoic acid containing from 2 through 8 carbon atoms, or mixture of such acids, the molar ratio of such acid or acids to the magnesium salt being from about 1.5 to about 20.3; contacting a hydroxy aldehyde having the formula

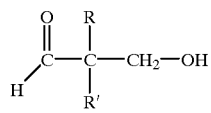

wherein R and R' are independently selected from $C_1$ through $C_4$ alkyl, with a catalytic amount of said catalyst liquid, under reaction conditions to form said dihydroxy ester.

12. The process of claim 1 wherein R and R' are simultaneously methyl.

13. The process of claim 2 wherein R and R' are simultaneously methyl.

14. The process of claim 3 wherein R and R' are simultaneously methyl.

15. The process of claim 4 wherein R and R' are simultaneously methyl.

16. The process of claim 5 wherein R and R' are simultaneously methyl.

17. The process of claim 6 wherein R and R' are simultaneously methyl.

18. The process of claim 7 wherein the hydroxy aldehyde is the crude product from the reaction of isobutyraldehyde and aqueous formaldehyde in the presence of a catalyst.

19. The process of claim 14 wherein hydroxypivalyl hydroxy-pivalate is recovered.

20. A process comprising heating crude hydroxypivaldehyde containing water in a drying zone at a temperature of from 50° C. to 150° C. and concurrently adding a catalytic amount of a liquid solution containing solubilized magnesium to the drying zone; separating water from the drying zone, and removing a hydroxypivaldehyde mixture having reduced water content and containing solubilized magnesium and hydroxypivalyl hydroxypivalate from the drying zone.

21. The process of claim 20 wherein the solubilized magnesium is supplied as magnesium isobutyrate, hydroxypivaldehyde mixture removed from the drying zone is passed to a reaction zone, and conversion is continued therein under reaction conditions to form hydroxypivalyl hydroxypivalate.

22. A process comprising heating crude hydroxypivaldehyde containing water in a drying zone at a temperature of from 50° C. to 150° C. and concurrently adding a catalytic amount of a liquid solution containing solubilized magnesium to the drying zone, separating water from the drying zone, and forming a first reaction liquid comprising hydroxypivaldehyde having reduced water content and containing solubilized magnesium and hydroxypivalyl hydroxypivalate; removing first reaction liquid from the drying zone and contacting removed first reaction liquid with a catalyst liquid containing additional solubilized magnesium in a reaction zone under reaction conditions to form hydroxypivalyl hydroxypivalate, and forming a second reaction liquid having a hydroxypivalyl hydroxypivalate content greater than the first reaction liquid.

23. The process of claim 21 wherein the crude hydroxypivaldehyde is formed by reacting isobutyraldehyde and aqueous formaldehyde in the presence of a catalyst.

24. The process of claim 22 wherein the crude hydroxypivaldehyde is formed by reacting isobutyraldehyde and aqueous formaldehyde in the presence of a catalyst.

25. The process of claim 21 wherein the liquid solution comprises from about 10 percent to about 60 percent magnesium isobutyrate and from about 90 percent to about 40 percent isobutyric acid, the molar ratio of isobutyric acid to magnesium isobutyrate being from about 1.5 to about 20.3.

26. The process of claim 24 wherein the catalyst liquid comprises from about 10 percent to about 60 percent magnesium isobutyrate and from about 90 percent to about 40 percent isobutyric acid, the molar ratio of isobutyric acid to magnesium isobutyrate being from about 1.5 to about 20.3.

* * * * *